United States Patent
Chong et al.

(10) Patent No.: US 12,311,006 B2
(45) Date of Patent: *May 27, 2025

(54) VAPORIZED MEDICANTS AND METHODS OF USE

(71) Applicant: CQENS Technologies Inc., Minneapolis, MN (US)

(72) Inventors: Alexander Chinhak Chong, St. Louis Park, MN (US); William P Bartkowski, Edina, MN (US); Marshall A Thompson, Camarillo, CA (US)

(73) Assignee: CQENS TECHNOLOGIES INC., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/133,410

(22) Filed: Apr. 11, 2023

(65) Prior Publication Data

US 2023/0241148 A1    Aug. 3, 2023

Related U.S. Application Data

(63) Continuation of application No. 17/174,725, filed on Feb. 12, 2021, now Pat. No. 11,622,985, which is a continuation of application No. 16/155,642, filed on Oct. 9, 2018, now Pat. No. 10,918,684, which is a continuation-in-part of application No. 15/880,872, filed on Jan. 26, 2018, now Pat. No. 10,758,582, which is a continuation-in-part of application No. 15/008,154, filed on Jan. 27, 2016, now Pat. No. 10,098,918, which is a continuation-in-part of application No. 14/937,737, filed on Nov. 10, 2015, now Pat. No. 9,770,408, which is a continuation-in-part of application No. 14/629,279, filed on Feb. 23, 2015, now Pat. No. 9,283,180, which is a continuation-in-part of application No. 13/653,320, filed on Oct. 16, 2012, now Pat. No. 8,962,040, which is a continuation-in-part of application No. 12/858,382, filed on Aug. 17, 2010, now Pat. No. 8,287,922, said application No. 14/937,737 is a continuation-in-part of application No. 13/846,617, filed on Mar. 18, 2013, now Pat. No. 9,254,002, which is a continuation-in-part of application No. 12/858,373, filed on Aug. 17, 2010, now abandoned.

(60) Provisional application No. 61/234,562, filed on Aug. 17, 2009, provisional application No. 61/234,560, filed on Aug. 17, 2009.

(51) Int. Cl.
| | | |
|---|---|---|
| A61K 36/00 | (2006.01) |
| A61K 9/00 | (2006.01) |
| A61K 31/475 | (2006.01) |
| A61K 31/485 | (2006.01) |
| A61K 31/7048 | (2006.01) |
| A61K 36/296 | (2006.01) |
| A61K 36/34 | (2006.01) |
| A61K 47/10 | (2017.01) |
| A61K 47/26 | (2006.01) |

(52) U.S. Cl.
CPC ............ *A61K 36/296* (2013.01); *A61K 9/007* (2013.01); *A61K 31/475* (2013.01); *A61K 31/485* (2013.01); *A61K 31/7048* (2013.01); *A61K 36/34* (2013.01); *A61K 47/10* (2013.01); *A61K 47/26* (2013.01); *A61K 2236/00* (2013.01)

(58) Field of Classification Search
CPC .................................................. A61K 31/485
See application file for complete search history.

(56) References Cited

U.S. PATENT DOCUMENTS

| | | | |
|---|---|---|---|
| 2004/0045546 A1* | 3/2004 | Hirsh | A61M 15/00 128/200.14 |
| 2006/0032496 A1* | 2/2006 | Hale | A61M 11/041 128/200.14 |
| 2007/0045288 A1 | 3/2007 | Nelson | |
| 2017/0119047 A1 | 5/2017 | Blandino | |
| 2021/0161984 A1 | 6/2021 | Chong et al. | |

FOREIGN PATENT DOCUMENTS

| | | |
|---|---|---|
| CN | 104095291 | 10/2014 |
| CN | 104664608 | 6/2015 |
| CN | 204949521 | 1/2016 |
| CN | 205648931 | 10/2016 |
| WO | WO2017068099 | 4/2017 |
| WO | WO2017109448 | 6/2017 |
| WO | WO2017186455 | 11/2017 |

* cited by examiner

*Primary Examiner* — Qiuwen Mi
(74) *Attorney, Agent, or Firm* — Cislo & Thomas, LLP

(57) ABSTRACT

A method and formulation for delivering a medication in a vaporized state using low temperatures to vaporize the formulation. The formulation contains an inert non-reactive compound that lowers the heat of vaporization of the formulation, and an alkaloid. The formulation may optionally contain glycerin, alcohol, and/or water. Examples of inert non-reactive compounds that can sufficiently lower the heat of vaporization of the formulation include propylene glycol, vegetable glycerin and polysorbate. The formulation can be vaporized using a hand-held low temperature vaporizer or atomizer.

18 Claims, No Drawings

VAPORIZED MEDICANTS AND METHODS OF USE

CROSS-REFERENCE TO RELATED APPLICATION

This patent application is continuation of U.S. patent application Ser. No. 17/174,725, filed Feb. 12, 2021, which is a continuation of U.S. patent application Ser. No. 16/155,642, filed on Oct. 9, 2018, which is a continuation-in-part of U.S. patent application Ser. No. 15/880,872, filed on Jan. 26, 2018 (now U.S. Pat. No. 10,758,582), which is a continuation-in-part of U.S. patent application Ser. No. 15/008,154, filed on Jan. 27, 2016 (now U.S. Pat. No. 10,098,918), which is a continuation-in-part of U.S. patent application Ser. No. 14/937,737, filed on Nov. 10, 2015 (now U.S. Pat. No. 9,770,408), which is a continuation-in-part of U.S. patent application Ser. No. 14/629,279, filed on Feb. 23, 2015 (now U.S. Pat. No. 9,283,180), which is a continuation-in-part of U.S. patent application Ser. No. 13/653,320, filed on Oct. 16, 2012 (now U.S. Pat. No. 8,962,040), which is a continuation-in-part of U.S. patent application Ser. No. 12/858,382, filed Aug. 17, 2010 (now U.S. Pat. No. 8,287,922), which claims the benefit of U.S. Provisional Patent Application No. 61/234,562, filed Aug. 17, 2009; U.S. patent application Ser. No. 14/937,737 is also a continuation-in-part application of U.S. patent application Ser. No. 13/846,617, filed Mar. 18, 2013 (now U.S. Pat. No. 9,254,002), which is a continuation-in-part of U.S. patent application Ser. No. 12/858,373 filed on Aug. 17, 2010 (now abandoned), which claims the benefit of U.S. Provisional Patent Application No. 61/234,560, filed Aug. 17, 2009, which applications are incorporated in their entirety here by this reference.

TECHNICAL FIELD

This invention relates to methods and formulations for vaporizing medicants and uses thereof.

BACKGROUND

When faced with a condition giving rise to bodily discomfort, such as a diseased state, disorder, ailment, normal bodily disruptions, and the like, most people turn to medication, such as drugs, supplements, herbs, and the like for immediate relief from the symptoms that arise from the underlying condition. There are certain legal and widely available over-the-counter (OTC) medications and supplements that have beneficial effects when used for a variety of common conditions. There are also certain controlled narcotics and pharmaceuticals prescribed by doctors for a variety of more serious conditions.

One of the most common routes of administration of these OTC and prescription drugs is oral administration. However, as with any oral delivery of medication, it must pass through the digestive tract. There are a number of disadvantages of oral administration. For example, because the drug has to pass through the digestive system, the onset of activation of the drug is slow. In addition, in the digestive tract the drug may be inactivated or destroyed, and therefore, lose its potency or efficacy. The drug itself can also cause problems in the digestive tract, or side effects, such as loss of appetite, diarrhea, acidity, and the like. Furthermore, patients may be reluctant or unable to swallow a pill.

Other routes of delivery exist, such as intradermal injections, patch applications, inhalations, and the like. Each of these has its own advantages and disadvantages. Therefore, there is still room for improving routes of administration of drugs.

For example, there are varieties of medicants which are safer, more effective, and more efficient with respect to efficacy if their ingestion is via inhalation of a vapor containing the medicant or its active ingredient rather than by gastrointestinal, intravenous or intramuscular delivery. However, most vaporization methodologies for inhalation are done at relatively high temperatures and, as a result, present risks or hurdles to either the efficacy of the medicant or the well-being of the user.

Certain medicants are intended to affect the brain or the brain's actions or activities but, given the accepted method of ingestion—gastrointestinal, intravenous, or intramuscular—these medicants can also have a variety of discomforting side effects due to the nature of ingestion or injection. These include, but are not limited to, gastro-intestinal complications, digestive disorders, high blood pressure, and/or headaches.

Additionally, certain methods to vaporize and deliver these medicants have drawbacks as well, specifically those that vaporize the medicant itself, changing the molecular or chemical structure of the medicant or those that vaporize an excipient at a high temperature, once again changing the molecular or chemical structure of the excipient and raising the risk of changing the chemical structure of the medicant when it interacts with the vaporized excipient.

In order to ensure that the medicant is delivered intact via inhalation it is critical that the method of vaporization does not change the chemical or fundamental molecular structure of the medicant or excipient. Therefore, there is still a need for improving the routes of administration of drugs. In particular, there is still a need for improving inhalers that can meter exact dosages without destroying the active ingredient.

SUMMARY

The invention of the present application discloses a method and formulation that can generate a vapor state of a medicant or active ingredient metered at precise dosages without destroying or damaging the medicant or active ingredient, or the excipient solution. In particular, a formulation has been devised in which the solution can be vaporized at a low, focused temperature that ensures vaporization of the excipient and not of the active ingredient; allowing for the inhalation of a specific, accurate serving or dose of the active ingredient via an inert excipient. Specifically, an excipient with a low vaporization temperature may be combined with an active ingredient that may have a higher vaporization temperature. In such a combination, the vaporizing excipient effectively acts as a carrier for the active ingredient. When the combination is heated to a temperature sufficient to vaporize the excipient, the excipient vapor carries molecules of the active ingredient along with it. Thus, the active ingredient is effectively "vaporized" at a temperature that is usually considerably lower than needed to vaporize the active ingredient alone.

In one embodiment, a method for medicant delivery is provided comprising: providing a medicant solution suitable for vaporization in a compact handheld device; providing the compact handheld device; vaporizing the medicant at a low temperature upon activation by a user such that an effective serving of the medicant is provided to the user.

In another embodiment, a medicant solution is provided for use in a vaporization delivery mechanism, the solution comprising: water; alcohol; an inert non-reactive compound; and an active ingredient. In some embodiments, the water and alcohol are optional. In some embodiments, the medicant solution may include glycerin (vegetable or otherwise) and/or flavoring. In some embodiments, the medicant solution may include polysorbates (polysorbate 20, 40, 60, 80, or others) and/or propylene glycol. The medicant solution is formulated such that it can be vaporized at a low temperature in a sufficient quantity to provide an effective serving of the active ingredient to a user.

The method and solution is designed to be used with a delivery device such as that described in U.S. patent application Ser. No. 13/453,939; Ser. No. 13/044,355; and 61/470,460 which applications are incorporated in their entirety here by this reference.

Accordingly, the method and formulation can be used to vaporize a variety of medicants, preferably, but not necessarily, medicants or active ingredients directed primarily toward neuro-activity. For example, these medicants or active ingredients include, but are not limited to, caffeine; alkaloids, such as yohimbine and codeine; hormones, such as melatonin and serotonin-classified; antihistamines, such as diphenhydramine; opioids, such as morphine and oxycodone; nootropics, such as piracetam; and amino acids, such as gamma-Aminobutyric acid (GABA), and tobacco constituents.

These medicants or active ingredients can be further classified by their consumer/patient use on a PRN (as needed) basis. These classes include 1) sleep aids—such as melatonin and gamma-Aminobutyric acid (GABA); 2) motion sickness antidote—such as diphenhydramine; 3) stimulants, such as energy and alertness aids—such as nicotine and caffeine; 4) analgesics—such as morphine, codeine and oxycodone; and, 5) sexual aids—such as yohimbine, icariin, and type-5 phosphodiesterase (PDE-5) inhibitors.

Other features and advantages of the present invention will become apparent from the following detailed description. It should be understood, however, that the detailed description and the specific examples, while indicating the preferred embodiments of the present invention, are given by way of illustration only, since various changes and modifications within the spirit and scope of the present invention will become apparent to those skilled in the art from this detailed description.

DETAILED DESCRIPTION OF THE INVENTION

The detailed description set forth below is intended as a description of presently-preferred embodiments of the invention and is not intended to represent the only forms in which the present invention may be constructed or utilized. The description sets forth the functions and the sequence of steps for constructing and operating the invention. It is to be understood, however, that the same or equivalent functions and sequences may be accomplished by different embodiments that are also intended to be encompassed within the spirit and scope of the invention.

In order to fully understand the manner in which the above-recited details and other advantages and objects according to the invention are obtained, a more detailed description of the invention will be rendered by reference to specific embodiments thereof.

In one embodiment, a medicant solution is provided comprising an excipient and an active ingredient or medicant (medicant and active ingredient are used interchangeably), in which the excipient can be vaporized at low temperatures relative to temperatures required by typical vaporizers. In another embodiment, a medicant delivery method is provided comprising providing a medicant solution that can be vaporized at low temperatures, and providing a device for vaporization of the medicant solution such that a user can absorb the vaporized solution via activation of the vaporization device to deliver an effective serving of medicant to a user.

While an effective serving, effective dose, or therapeutically effective amount of a medicant may vary depending upon the particular physiology of the user, for example, the user's weight or body make-up, as used herein, the phrases effective serving, effective dose, and therapeutically effective amount (used interchangeably) means an amount sufficient such that the user experiences the intended positive effects experienced when the medicant is delivered through other known methods. In one aspect of this embodiment the effective serving can be delivered in as little as one activation of the delivery device by the user, and in other aspects the effective serving may be delivered through multiple activations of the delivery device by the user over 1, 2, 3, 4, 5, 6, 7, 8, 9, 10 or more minutes of use in a manner similar to the use associated with using a portable, handheld aerosol breath freshener.

Alternatively, the effective serving can be delivered over a specified number of activations of the delivery device by the user. Further, the number of activations can occur over a specified time period. For example, delivery of an effective serving can be provided with 1, 2, 3, 4, 5, 6, 7, 8, 9, 10, 11, 12, 13, 14, 15, 16, 17, 18, 19, or 20 activations. For example, the effective dose may be delivered in 1-20 activations, 5-15 activations, 12-20 activations, 12-18 activations or about 15 activations, any of which can occur in a 1, 2, 3, 4, 5, 6, 7, 8, 9, 10, or 20 minute period. Some embodiments will be formulated and/or configured such that the effective dose is delivered as quickly as possible, and other embodiments can be formulated and/or configured such that the effective dose is delivered in about the same time and manner as if one were using a portable, handheld aerosol breath freshener.

In various embodiments, a single serving may be delivered in less than 50 activations, about 1-50 activations, about 1-20 activations, about 5-15 activations or about 8-10 activations. The single serving may include greater than about 0.5 mg, from about 0.5 mg to about 100 mg, from about 0.5 mg to about 50 mg, from about 0.5 mg to about 20 mg, from about 0.5 to about 10 mg, from about 5 mg to about 10 mg, or about 5 mg.

The formulation of the medicant solution comprises an active ingredient and an excipient capable of vaporizing at low temperatures. When the medicant solution is heated, the excipient vaporizes at a relatively low temperature, carrying the active ingredient with it. Even though the active ingredient may have a higher vaporization temperature, the excipient vapor transports molecules of the active ingredient, delivering the active ingredient to the user at a low temperature.

The active ingredient may be approximately 0.5% or more of the medicant solution with the remainder of the medicant solution comprising the excipient. An acceptable range of active ingredient in the medicant solution ranges from about 0.5% to about 99% or about 0.5% to about 50% of the medicant solution. A medicant solution comprising about 0.5% to about 20% of the active ingredient is also acceptable. Preferably, the medicant solution comprises between about 0.5% to about 15% of the active ingredient. More preferably, the medicant solution comprises about 5% to about 10% active ingredient. Most preferably, the medicant solution comprises about 5% active ingredient. The remainder of the medicant solution may be comprised of the excipient.

The excipient may comprise one or more of an inert non-reactive compound, e.g., propylene glycol, polysorbate, and/or glycerin, such that the medicant solution can be vaporized at low temperatures for activation by a user. In some embodiments, the excipient may further comprise water and/or alcohol. In some embodiments, water is present at a concentration of about 0.01% to about 30% of the excipient. Preferably, water is present at about 0.01% to about 20% of the excipient. More preferably, water is present at about 2% to about 18% of the excipient. More preferably, water is present at about 5% to about 15%. Most preferably, water is present at about 10% of the excipient.

In some embodiments, alcohol is present at a concentration of about 0.01% to about 30% of the excipient. Preferably, alcohol is present at about 0.01% to about 20% of the excipient. More preferably, alcohol is present at about 2% to about 18%. More preferably, alcohol is present at about 5% to about 15%. Most preferably, alcohol is present at about 10% of the excipient.

In some embodiments, propylene glycol, polysorbate, and/or glycerin can be used alone or in any combination thereof as the excipient.

In some embodiments, the excipient may comprise propylene glycol. Propylene glycol may be present at about 1% to about 30% of the excipient. In some embodiments, propylene glycol is present at about 5% to about 20%. In some embodiments, propylene glycol is present at about 5% to about 15% or about 10% to about 15%. In some embodiments, propylene glycol may be present at concentrations of at least 70% of the excipient. In some embodiments, propylene glycol may be present at concentrations of at least 85% of the excipient. In some embodiments, propylene glycol can make up the entire excipient to which the active ingredient may be added. Therefore, propylene glycol can make up at least about 1% of the excipient, at least about 5% of the excipient, at least about 10% of the excipient, at least about 15% of the excipient, at least about 20% of the excipient, at least about 30% of the excipient, or more.

In another aspect of the invention, the excipient may comprise glycerin, such as vegetable glycerin. In some embodiments, glycerin may be present at about 1% to about 30% of the excipient. In some embodiments, glycerin may be present at about 5% to about 20% of the excipient. In some embodiments, glycerin may be present at about 5% to about 10% or about 10% to about 15% of the excipient. In some embodiments, glycerin may be present at concentrations of at least about 70% of the excipient. In some embodiments, glycerin may be present at concentrations of at least about 85% of the excipient. Therefore, glycerin can make up at least about 1% of the excipient, at least about 5% of the excipient, at least about 10% of the excipient, at least about 15% of the excipient, at least about 20% of the excipient, at least about 30% of the excipient, or more. In some embodiments, glycerin can make up the entire composition of the excipient to which the active ingredient may be added. Without being limited by theory, it is believed that the addition of glycerin provides a more robust vapor upon vaporization of the product.

In some embodiments, the excipient may comprise a compound from the polysorbate class or family, such as polysorbate 20 (polyoxyethylene sorbitan monolaurate), polysorbate 40 (polyoxyethylene (20) sorbitan monopalmitate), polysorbate 60 (polyoxyethylene sorbitan monostearate), and polysorbate 80 (polyoxyethylene sorbitan monooleate).

The polysorbate compound used in the excipient may be polysorbate 20, polysorbate 40, polysorbate 60, polysorbate 80, or a polysorbate composition comprising any combination thereof. The type of polysorbate used or the combination of polysorbates used depends on the intended effect desired as the different polysorbates offer different attributes due to the different molecule sizes of the different polysorbate. For example, the polysorbate molecules increase in size from polysorbate 20 to polysorbate 80. There is a sliding scale effect of vapor amount or density and lung penetration with increasing size of polysorbate molecules. Using smaller size polysorbate molecules creates less of a vapor, but permits deeper lung penetration. This may be desirable when the user is out in public where he would not want to create a large plume of "smoke" (i.e. vapors). This effect can be achieved, for example, if the excipient comprises about 70% to about 100% polysorbate 20 or polysorbate 40.

Conversely, if a dense vapor is desired, then the larger polysorbate molecules, such as polysorbate 80 or polysorbate 60, can predominate the polysorbate composition used in the excipient. For example, the polysorbate composition may comprise about 70% to about 100% polysorbate 80 or polysorbate 60. Therefore, characteristics, features, and attributes of the medicant solution and the resultant vapor can be controlled by using a polysorbate composition with a specific combination of polysorbate 20, polysorbate 40, polysorbate 60, and/or polysorbate 80.

Polysorbate, meaning any polysorbate from the polysorbate family, and any combination thereof, may be present at about 1% to about 30% of the excipient. In some embodiments, polysorbate is present at about 5% to about 20% of the excipient. In some embodiments, polysorbate is present at about 5% to about 15% or about 10% to about 15% of the excipient. In some embodiments, polysorbate may be present at concentrations of at least 70% of the excipient. In some embodiments, polysorbate may be present at concentrations of at least 85% of the excipient. In some embodiments, polysorbate can make up the entire excipient to which the active ingredient may be added. Therefore, polysorbate can make up at least about 1% of the excipient, at least about 5% of the excipient, at least about 10% of the excipient, at least about 15% of the excipient, at least about 20% of the excipient, at least about 30% of the excipient, or more. Without being bound by theory, it is believed that polysorbate provides a more robust vapor upon vaporization, reduces the heat of vaporization, and produces smaller vapor molecules, thereby achieving deeper lung penetration upon inhalation.

In another aspect of this invention, the medicant solution further comprises flavoring.

The medicant solution is formulated such that an effective serving of the active ingredient can be delivered to a user in a specified time period when the medicant solution is vaporized and inhaled by the user. In one aspect of this embodiment the effective serving can be delivered over a specified time period when the solution is vaporized without the addition of heat.

Depending on the form of the active ingredient the medicant solution may be prepared by combining a tincture of an active ingredient with the excipient. In some embodiments, the medicant solution may be prepared by contacting the active ingredient with the excipient. In other words, the medicant solution is prepared by extracting the active ingredient from its source (for example, herbs, plants, roots, etc.)

with the excipient. The final concentration of the active ingredient may be controlled by the time, temperature, and pressure at which the source is in contact with the excipient.

Active ingredients may be extracted from their respective sources by a variety of methods. For example, to promote leaching of the active ingredient from its source, various methods may be employed to contact the source with the excipient, including maximizing the surface area of the source. In one embodiment, the source is formed in the shape of a mesh screen through which the excipient is passed. While the excipient is passed through the source, the active ingredient is extracted from the source into the excipient. In other configurations, the source is formed to provide the maximum surface area for contact with the excipient yet still allow flow of the excipient through the source and into a vaporization device. Examples of other configurations for use in maximizing the surface area of the source for contact with the excipient include spirally winding the source, converting the source into pellets, converting the source into powder, or encapsulating the source in a porous, filter-like material, which will allow the excipient to flow through the source-encapsulate allowing the active ingredient to leach into the excipient from its source. Leaching, or extraction in general, may also be promoted through modifying the temperature of the excipient or the pressure under which the excipient is contacted with the source.

In some embodiments the excipient and the medicant source are contacted immediately prior to vaporization. In other embodiments the excipient and medicant source can be contacted over an extended period of time prior to vaporization. For example, the medicant source can be provided immersed in the excipient such that the excipient has been in contact with the medic ant source for an extended period of time prior to vaporization. In such examples, the leaching or extraction of the active ingredient can be promoted by varying the conditions or other parameters during contact of the excipient with the medicant source. The medicant source can be removed from the formed medicant solution prior to providing the medicant solution to the end consumer for inclusion in a device for vaporization, or immediately prior to vaporization by draining the medicant solution from the medicant source.

The medicant solution is then vaporized by activation of a vaporization or delivery device by the user. Examples of vaporizers (particularly, hand-held low temperature vaporizer) or delivery devices that may be used to vaporize the medicant solution are disclosed in U.S. patent application Ser. No. 10/587,707; Ser. No. 10/547,244; Ser. No. 13/453,939; Ser. No. 13/044,355; 61/470,460, incorporated herein by reference. Other devices may be used, which include atomizers or other vaporizers known in the art or combinations thereof. Vaporization or atomization can be performed with or without the addition of heat to the solution. For example, the solution to be vaporized can first be atomized providing for ease of vaporization without the addition of heat. In one aspect a low temperature vaporizer is provided.

The temperatures referred to in this application refer to the temperature of the heating element of a vaporizer that contacts the medicant for vaporization or the temperatures at which the medicants are vaporized. Low temperature means a temperature for vaporizing a medicant that is lower than traditional temperatures used for vaporizing medicants. For example, traditional temperatures rely on heating elements that reach 300 degrees Celsius (C) or higher for vaporizing liquids. Therefore, low temperatures mean temperatures less than or equal to approximately 280 degrees C., and preferably less than or equal to approximately 250 degrees C. In some embodiments, low temperatures are from approximately 90 degrees C. to approximately 280 degrees C. In some embodiments, low temperatures may be from approximately 180 degrees C. to approximately 250 degrees C. In some embodiments, low temperatures may be from approximately 180 degrees C. to approximately 225 degrees C. In some embodiments, low temperatures may be from approximately 180 degrees C. to approximately 200 degrees C.

As indicated above, low temperatures also refer to the heat of vaporization of the medicant solution, where the heat of vaporization means the temperature at which the medicant solution vaporizes from a liquid state to a gaseous state. Therefore, the heat of vaporization for the medicant solution (e.g., the temperature the heating element of the vaporizer must reach to vaporize the medicant) may be from approximately 90 degrees C. to approximately 280 degrees C. In some embodiments, the heat of vaporization for the medicant solution is from approximately 180 degrees C. to approximately 250 degrees C. In some embodiments, the heat of vaporization for the medicant solution is from approximately 180 degrees C. to approximately 225 degrees C. In some embodiments, the heat of vaporization may be from approximately 180 degrees C. to approximately 200 degrees C.

In some embodiments, an excipient with a lower heat of vaporization may be used, including but not limited to excipients comprising polysorbate. In such embodiments, low temperatures for vaporization may be from approximately 90 degrees C. to approximately 200 degrees C., from approximately 90 degrees C. to approximately 180 degrees C., from approximately 90 degrees C. to approximately 160 degrees C., from approximately 90 degrees C. to approximately 150 degrees C., from approximately 90 degrees C. to approximately 140 degrees C., or from approximately 90 degrees C. to approximately 120 degrees C., and any temperatures therebetween.

In embodiments in which propylene glycol is used as the excipient, low temperatures for vaporization may be from approximately 90 degrees C. to approximately 250 degrees C., from approximately 110 degrees C. to approximately 225 degrees C., from approximately 150 degrees C. to approximately 210 degrees C., or from approximately 170 degrees C. to approximately 200 degrees C., and any temperatures therebetween.

In embodiments in which vegetable glycerin is used as the excipient, low temperatures for vaporization may be from approximately 90 degrees C. to approximately 280 degrees C., from approximately, 110 degrees C. to approximately 280 degrees C., from approximately 150 degrees C. to approximately 280 degrees C., from approximately 200 degrees C. to approximately 280 degrees C., from approximately 225 degrees C. to approximately 280 degrees C., or from approximately 250 degrees C. to approximately 280 degrees C., and any temperatures therebetween.

Therefore, depending on the composition of the excipient, low temperatures can range from as low as 90 degrees C. up to 280 degrees C. and any temperature therebetween.

In another embodiment, a device for implementing the medicant delivery methods set forth herein is provided comprising a shell, a mouthpiece, an air inlet provided on the external wall of the shell, a cell, an electronic circuit board, a normal pressure cavity, a sensor, an atomizer, a solution reservoir, a medicant reservoir, a solution stream passage, a negative pressure cavity provided in the sensor, an atomization cavity arranged in the atomizer, and an aerosol passage, wherein the solution reservoir is in contact with the medicant reservoir and the atomizer, and the air inlet, normal pressure cavity, atomizer, aerosol passage, gas vent and mouthpiece are interconnected.

In another embodiment, a device for implementing the medicant delivery methods set forth herein is provided comprising a shell, a mouthpiece, an air inlet provided on the external wall of the shell, a cell, an electronic circuit board, a normal pressure cavity, a sensor, an atomizer, a solution reservoir, a solution stream passage, a negative pressure cavity provided in the sensor, an atomization cavity arranged in the atomizer, and an aerosol passage, wherein the solution reservoir is in contact with the atomizer, and the air inlet, normal pressure cavity, atomizer, aerosol passage, gas vent and mouthpiece are interconnected. The solution reservoir may be configured to retain a medicant solution and medicant, or medicant solution that has previous been contacted with medicant.

In some embodiments the device is provided in the configuration of a cigar or cigarette. In other embodiments the device is provided in other configurations such that the device can be readily distinguished from a cigar or cigarette.

In some embodiments, the delivery device is a hand-held, personal portable device that is disposable. Moreover, in some embodiments the method of vaporization uses low temperatures to vaporize the medicant solution.

In another embodiment a disposable cartridge is provided comprising a medicant solution or medicant (or active ingredient) and an excipient as set forth herein. The cartridge can include one or more servings of medicant as set forth herein. In one aspect of this embodiment the cartridge can include between about 5-50 servings, between about 5-25 servings, between about 10-25 servings, between about 10-50 servings, between about 10-20 servings of medicant.

Ingestion via vapor inhalation provides effects within 30 to 90 seconds. The quick, efficient method of inhalation ingestion provides for lower doses and significantly minimizes the risk of over dosing and its attendant complications, as the effects are almost immediately felt. This reduces the tendency to take more medication before the effects have set on as in the case of orally ingested drugs that are absorbed through the digestive tract. Accordingly, the invention of the present application provides users with an easy-to-use, convenient medicant product.

EXAMPLES

Examples of medicants or active ingredients that can be used with the present invention include, but are not limited to, nicotine and other tobacco constituents; caffeine; alkaloids, such as yohimbine and codeine; hormones, such as melatonin and serotonin-classified; antihistamines, such as diphenhydramine; opioids, such as morphine and oxycodone; nootropics, such as piracetam; amino acids, such as gamma-Aminibutyric acid (GABA); plants and herbs, such as green tea, hoodia, yohimbine, and epimedium; and compounds involved in signal transduction pathways, such as type-5 phosphodiesterase (PDE-5) inhibitors.

These and any other active ingredients can be used as stimulants, alertness aids, cognitive enhancers, sleep aids, motion sickness antidotes, analgesics, sexual aids, and other conditions known to be treatable with these active ingredients.

Tobacco Constituents

Smokers of traditional tobacco products, for example, cigarettes, cigars and pipes, are finding that their use of these products has been significantly and seriously curtailed by smoking regulations passed and enacted due to concerns about the public health dangers of second hand smoke, and potentially harmful chemicals found in the smoke, including tar and carbon monoxide.

In addition to traditional tobacco alternatives to those that must be ignited, cigarettes, cigars ad pipes, like snuff, snus, chewing tobacco, tobacco tablets, tobacco lozenges and tobacco strips, smokers recently have also be utilizing electronic nicotine delivery devices or e-cigarettes. These products vaporize nicotine, allowing a smoker to inhale a nicotine-infused vapor in a manner similar to smoking.

However, nicotine is just one constituent of tobacco that provides satisfaction to smokers. There are a number of others—actual tobacco flavor, aroma, and monoamine oxidase inhibitors. As used herein, desired tobacco constituent means one or more of tobacco flavor, aroma, monoamine oxidase inhibitors, and nicotine.

Monoamine oxidase inhibitors ("MAOIs") are naturally found in tobacco and naturally occur in tobacco smoke. These naturally occurring tobacco constituents are also used in anti-depressants and are widely acknowledged to be mood elevators.

While there have been inventions that teach as to using actual leaf tobacco in certain combinations that then vaporize the constituents without ignition, they combine tobacco in certain and specific forms with solutions that require heating to a temperature range of at least 200 degrees C.

As used in this application, a "first solution" is an excipient solution prior to its contact with an active, such as tobacco to form a "tobacco solution." In some circumstances, a first solution may have had previous tobacco contact, but will eventually have subsequent tobacco contact to form a "tobacco solution."

Vaporization at 200 degrees C. represents a relatively low temperature compared to other current e-cigarettes, but there are compelling reasons for seeking first solutions (i.e. excipient solutions) that vaporize at much lower temperatures. These reasons include a) minimizing power needs to reach temperatures of less than 200 degrees C., allowing for safer and more efficiently powered devices; and, b) using first solutions comprised of smaller molecules, allowing for deeper lung penetration upon inhalation and more efficacious absorption of the tobacco constituents, which, in turn, will allow for more efficient use of tobacco and its constituents—which would be beneficial and desirable should governmental authorities determine that e-cigarettes need to be limited with respect to the volume of tobacco or the density of nicotine and/or other constituents provided in a commercially-available product/device. Those potential limitations notwithstanding, low temperature vaporization of tobacco formulations using first solutions with smaller molecules than currently being utilized and vaporization points well under 200 degrees C. will prove to be more effective and efficacious with respect to providing a safer alternative to the public health risks associated with traditional tobacco products intended to be ignited and smoked.

Accordingly, there is a need in the art for a more effective and safer tobacco delivery mechanism and method of use that provides for vaporization at temperatures well under 200 degrees C. and, ideally, at no more than 100 degrees C.

In one embodiment of the present invention a method for tobacco delivery is provided comprising: providing tobacco; providing a first solution; contacting the tobacco with the first solution to form a tobacco solution comprising tobacco constituents; and vaporizing the tobacco solution. In other aspects of this embodiment the step of vaporizing the tobacco solution comprises using a piezoelectric element to atomize the tobacco solution without the addition of heat and the tobacco constituents comprise nicotine and at least one monoamine oxidase inhibitor derived from tobacco. In another aspect of this embodiment, the step of vaporizing the tobacco solution comprises using a low temperature vaporizer to vaporize the tobacco solution and the tobacco constituents comprise nicotine and at least one monoamine oxidase inhibitor derived from tobacco. These steps could be used independently or combined, such as atomizing the solution and then vaporizing it.

In another embodiment of the present invention a tobacco solution for use in a vaporization delivery mechanism is provided comprising: water; alcohol; propylene glycol; and tobacco constituents. In one aspect of this embodiment the tobacco constituents comprise nicotine and at least one monoamine oxidase inhibitor derived from tobacco.

In another embodiment of the present invention a device for tobacco delivery is provided comprising: a first solution reservoir comprising a first solution; tobacco; a vaporization mechanism, wherein the solution is contacted with the tobacco to form a tobacco solution comprising tobacco constituents, and wherein the tobacco solution is then provided to the vaporization mechanism. In one aspect of this embodiment the vaporization mechanism comprises a piezoelectric element to atomize the tobacco solution without the addition of heat. In another aspect of this embodiment the vaporization mechanism comprises a low temperature element to vaporize the tobacco solution at a low temperature. In another aspect of this embodiment the tobacco constituents comprise nicotine and at least one monoamine oxidase inhibitor derived from tobacco.

In another embodiment of the present invention, a tobacco solution is provided prepared by a process comprising the steps of: providing tobacco; providing a first solution comprising water, alcohol, and propylene glycol; contacting the first solution with the tobacco to form a tobacco solution comprising tobacco constituents. In one aspect of this embodiment, the step of contacting the first solution with the tobacco to form a tobacco solution comprises immersing the tobacco in the first solution for a time sufficient to extract the tobacco constituents from the tobacco. In another aspect of this embodiment, the tobacco constituents comprise nicotine and at least one monoamine oxidase inhibitor derived from tobacco. In another aspect of this embodiment, the first solution further comprises glycerin.

In another embodiment of the present invention, the alcohol, polypropylene glycol, and/or glycerin from the tobacco solution are replaced with one or more of the polysorbate family of compounds—polysorbate 20 (polyoxyethylene sorbitan monolaurate), polysorbate 40 (polyoxyethylene (20) sorbitan monopalmitate), polysorbate 60 (polyoxyethylene sorbitan monostearate) and polysorbate 80 (polyoxyethylene sorbitan monooleate.) All members of the polysorbate family have much smaller molecules than those of other well-known excipients in e-cigarettes—propylene glycol, vegetable glycerin, etc. Additionally, all members of the family have vaporization temperatures (boiling points) at 100 degrees C. and flash points at 137 degrees C. Current technology in e-cigarette devices, using their method of vaporization and a power source that is essentially uncontrolled (i.e. lithium batteries that are controlled by external forces, rather than by battery capacity and state of charge), do not have the ability to limit the heat of the vaporizing element to 100 degrees C. and will always run the risk of heating the solution well past the flash point of 137 degrees C., thereby essentially breaking the molecule and causing fundamental molecular changes in the excipient and in the solution. Additionally, the vapor molecule of the polysorbate is much smaller than that of propylene glycol and vegetable glycerin and, in theory, should be able to achieve deeper lung penetration than those excipients, requiring a smaller amount of active ingredients—tobacco constituents—to achieve efficacious results.

For example, one activation of a device used with the current method can deliver the equivalent desired tobacco constituents from one puff from a typical tobacco cigarette. In other embodiments, one activation may be configured to deliver 1, 2, 3, 4, 5, 10, 20, 30, 40, 50, 60, 70, 80, or 90 percent of the desired tobacco constituents from one puff of a tobacco cigarette. Such embodiments are described as delivering a percentage of the effect serving of one or more desired tobacco constituents. In one aspect of this embodiment, the method delivers a specified percentage, e.g., 1, 2, 3, 4, 5, 10, 20, 30, 40, 50, 60, 70, 80, or 90 percent, of tobacco flavor, aroma, monoamine oxidase inhibitors, nicotine, or any other target constituent or combination thereof, in a single serving.

The solution may be any solution sufficient to allow the constituents of the tobacco to leach or be extracted into the solution upon contact with the fibrous tobacco for a specified time period to form a tobacco solution. Examples of suitable solutions include one or more of water, alcohol, and an inert non-reactive compound, for example propylene glycol. The solution can comprise about 0.01% to about 20% water, about 2% to about 18% water, about 5% to about 15% water, or about 10% water; about 0.01% to about 20% alcohol, about 2% to about 18% alcohol, about 5 to about 15% alcohol, or about 10% alcohol, with the balance being propylene glycol. In another aspect of this embodiment, the solution further comprises glycerin, including from about 1% to about 30%, about 5 to about 20%, about 5% to about 10%, or about 10% to about 15% glycerin.

Without being limited by theory, it is believed that the addition of glycerin provides a more robust vapor upon vaporization of the product and promotes the extraction or leaching of nicotine and other desirable components from the tobacco.

In tobacco solutions using polysorbates, the effective serving or portion of tobacco constituents may be approximately 0.5% or more of the tobacco solution. An acceptable range of tobacco constituents in the tobacco solution ranges from about 0.5% to about 99% or about 0.5% to about 50% of the tobacco solution. A tobacco solution comprising about 0.5% to about 20% tobacco constituents is also acceptable. Preferably, the tobacco solution comprises between about 0.5% to about 15% tobacco constituents. More preferably, the tobacco solution comprises about 5% to about 10% tobacco constituents. Most preferably, the tobacco solution comprises about 5% tobacco constituents.

The polysorbates make up the remainder of the tobacco solution. Therefore, the tobacco solution can comprise up to 99.5% of polysorbate.

Some embodiments provided herein produce a vapor containing the key constituents of tobacco that smokers find most appealing, comforting and satisfying without many of the harmful components created through burning the tobacco.

In another embodiment, a tobacco solution is provided for use in the methods and devices disclosed herein. The tobacco solution comprises actual tobacco constituents, including nicotine, flavor, aroma and MAOIs. The tobacco solution may be formed by contacting a solution as set forth herein with tobacco as set forth herein to form a tobacco solution. The concentration of the actual tobacco constituents of the tobacco solution can be varied by varying the method for making the tobacco solution. For example, one can vary the contact time between the solution and the tobacco, the temperature at which the contact occurs, or the pressure at which the contact occurs. The tobacco solution may be provided with or without tobacco in contact with the tobacco solution.

Stimulants and Cognitive Enhancers

Caffeine is an alkaloid, a bitter substance found in coffee, tea, soft drinks, chocolate, kola nuts, and certain medicines. It has many effects on the body's metabolism, including stimulating the central nervous system. This makes the consumer more alert and provides a boost of energy. Accordingly, caffeine may be used as the medicant in the invention of the present application.

Sleep Aids

Diphenhydramine is a first generation antihistamine mainly used to treat allergies and available in over the counter, non-prescriptive medications like Benadryl. Like most other first generation antihistamines, the drug also has a powerful hypnotic effect, and for this reason is often used as a non-prescription sleep aid. Diphenhydramine is thought to block the re-uptake of histamine neurotransmitters, thereby causing histamine to build up in the spaces called synapses that are present between nerve cells. This leads to sedative effects. Diphenhydramine works both centrally within the brain as well as in peripheral nerve cells in other parts of the body. It possesses other effects and can counter nausea due to motion sickness.

Among the traditional methods for ingesting diphenhydramine as a sleep aid is by mouth in various and readily available digestible compounds. It would be more effective, quicker acting and less likely to cause gastro-intestinal distress or discomfort if diphenhydramine were more quickly transported to the brain through the cardio-pulmonary system by ingesting and inhaling a vaporized product containing Diphenhydramine. A fast-acting diphenhydramine may be particularly useful for relieving motion sickness in progress, or as a sleep aid taken at or after bedtime. Accordingly, Diphenhydramine may be used as the medicant in the invention of the present application.

Doxylamine is also a first generation antihistamine often used as a sleep aid. Doxylamine is a member of the ethanolamine class of antihistamines and has significant anti-allergy properties. As a sleep aid it works by depressing the central nervous system to produce drowsiness. Doxylamine succinate is used in certain formulations of the over-the-counter products Unisom and Nyquil, and could be implemented in the invention according to the methods described above for Diphenhydramine and for similar uses. Accordingly, doxylamine could also be used as the medicant in the invention of the present application.

Melatonin is a naturally occurring compound, a hormone, found in animals, plants, and microbes. In animals, melatonin is made by the pineal gland, a small gland in the brain. Very small amounts of it are found in foods such as meats, grains, fruits, and vegetables. It can be purchased as a dietary supplement.

Circulating levels of melatonin vary in a daily cycle, thereby regulating the circadian rhythms of several biological functions, including controlling the sleep wake cycles. Many biological effects of melatonin are produced through activation of melatonin receptors, while others are due to its role as a pervasive and powerful antioxidant, with a particular role in the protection of nuclear and mitochondrial DNA.

Today, melatonin is used for a variety of purposes, but most often used for human sleep enhancement by regulating the sleep-wake cycle by causing drowsiness and lowering body temperature and affecting the central nervous system.

Among the traditional methods or ingesting melatonin is by mouth in various and readily available digestible compounds. When used as a sleep aid, melatonin is typically taken 30-60 minutes prior to bedtime, to allow the melatonin time to dissolve in the stomach and absorb into the blood stream to take effect. It would be more effective, quicker acting and less likely to cause gastro-intestinal distress or discomfort if melatonin were more quickly transported to the brain through the cardio-pulmonary system by ingesting and inhaling a vaporized product containing melatonin. A quick-acting melatonin would be particularly helpful as a sleep aid when taken at or after bedtime. Accordingly, melatonin may be used as the medicant in the present application.

Valerian (*Valeriana officinalis*, Caprifoliaceae) is a perennial flowering plant, which has long been used as a medicinal herb, including as a sleep aid. The root of the plant and its extracts are most often used as a sleep aid. Typical preparations sold as dietary supplements include capsules with dried root, and an extract of the essential oil. Research is not conclusive, but it is thought to interact with the GABA receptor. Compounds known to be in valerian that may contribute to its method of action include Alkaloids: actinidine, chatinine, shyanthine, valerianine, and valerine, Gamma-aminobutyric acid (GABA), Isovaleric acid, Iridoids, including valepotriates: isovaltrate and valtrate, Sesquiterpenes (contained in the volatile oil): valerenic acid, hydroxyvalerenic acid and acetoxyvalerenic acid, and Flavanones: hesperidin, 6-methylapigenin, and linarin. Accordingly, valerian could also be used as the medicant in the invention of the present application.

Analgesics

Analgesics may also be used as a medicant in the present application. GABA is traditionally known as an inhibitory neurotransmitter involved in regulating neuronal communications through GABA receptors. GABA is naturally occurring in the human body. Supplementing a diet with GABA may have various benefits, including but not limited to analgesic benefits. Accordingly, GABA may be used as the medicant in the present application.

Opioids are recognized as the benchmark of the class of analgesics used to relieve or to manage severe or agonizing pain and suffering. Although opioids are substances that act in a similar way as opiates, for the purposes of this application, the term opioid and opioids will include and encompass opiates. Therefore, opiates are of the opioid class of drugs and are analgesic alkaloid compounds found naturally in the opium poppy plant. Opiates can be classified as follows: natural opiates, semi-synthetic opiates and synthetic opiates. Examples of natural opiates are morphine, codeine, and thebaine. Examples of semisynthetic opiates include heroin, hydrocodone, hydromorphone, oxycodone, and oxymorphone. Synthetic opiates include fentanyl, buprenorphine, and methadone. All opioids, including the opiates, are considered drugs of high abuse potential and are listed under the Controlled Substances Act.

In addition to being controlled substances and having high abuse potential, opioids, when administered under the care of a physician and subject to all relevant pharmaceutical and regulatory mandates, generally are delivered orally or by intravenous injection, traveling, in first case, through the gastro-intestinal tract, then through the blood stream, and to the central nervous system. These forms of delivery have significant side-effects, which include, but are not limited to, gastro-intestinal distress, itching, nausea, vomiting, drowsiness, dry mouth, miosis, orthostatic hypotension, urinary retention, depression and constipation.

One of the earliest forms of opiate ingestion was through inhalation—in the earliest form, through igniting a natural opiate and inhaling the smoke produced. Inhalation of the opiate avoids the gastro-intestinal tract—and, as a result, avoids many of the most common side-effects, transports through the cardio-pulmonary tract, and delivers its analgesic effects much quicker and more efficiently. However, smoking and the inhaling is inexact and impossible to dose or prescribe in an efficacious manner.

Certain vaporizing technologies (such as those described in U.S. Pat. No. 8,903,228, U.S. patent application Ser. No. 14/004,150, and U.S. application Ser. No. 13/453,939, which applications are incorporated here by this reference in their entirety) now allow for accurate dosing and for controlled temperature of the heating element being used to vaporize. These technologies also could offer safeguards as to authentication and verification of the user before dispensing, and are designed so as to be impossible to contaminate, adulterate or misappropriate; or for the user to administer at times other than prescribed and, or more often, than in specific time periods other than those prescribed.

These vaporizing technologies combine the opiate with an excipient. For example, the excipient may comprise a polysorbate, inclusive of polysorbates 20, 40, 60 and 80, propylene glycol ("PG"), or vegetable glycerin ("VG"). These excipients vaporize at relatively low temperatures. For example, on the low end, excipients comprising polysorbates may vaporize at temperatures of about 90 degrees C. or 100 degrees C. up to about 200 degrees C. On the high end, excipients comprising PG and/or VG may vaporize at temperatures up to approximately 250 degrees C. or approximately 280 degrees C.

In some embodiments, the temperature for vaporizing any of the medicants can be as high as 385 degrees C. Therefore, the temperature for vaporizing medicants can range from approximately 90 degrees C. to approximately 385 degrees C. For example, the opioid-containing medicants can be vaporized at temperatures from approximately 330 degrees C. to approximately 385 degrees C. Preferably, the temperature may be from approximately 340 degrees C. to approximately 380 degrees C. More preferably, the temperature may be from approximately 370 degrees C. to approximately 380 degrees C.

Given the side-effects and risks associated with the most common methods of opiate delivery and the additional risks of abuse and subsequent recovery; and given the systemic societal cost of regulating, policing and rehabilitating those who have come to abuse and those who work outside the regulations to encourage such abuse, there is a need in the art for formulations that can be vaporized by devices designed to deliver more safely, more effectively and more securely, ensuring accurate dosages, verified and prescribed users and proper self-administration by the user—at no more than prescribed daily dosages and at the prescribed times.

The following detailed description of certain opioids is not meant to be limiting; any opioid could be used as a medicant in the present application. Morphine is highly regarded as an analgesic to relieve severe or agonizing pain and suffering. Morphine is the most abundant alkaloid found in opium. Like other opioids, e.g. morphine (OxyContin, Percocet, Percodan), hydromorphone (Dilaudid, Palladone), and diacetylmorphine (heroin), morphine acts directly on the central nervous system (CNS) to relieve pain. Among the traditional methods or ingesting morphine is by intravenous injection, traveling through the blood stream to the central nervous system. Morphine has a high potential for addiction; tolerance and psychological dependence develop rapidly. It would be more effective, quicker acting and less likely to cause gastro-intestinal distress or side effects such as itching, nausea, vomiting, drowsiness, dry mouth, miosis, orthostatic hypotension, urinary retention, depression and constipation if morphine was more quickly transported to the brain through the cardio-pulmonary system by ingesting and inhaling a vaporized product containing morphine. Accordingly, morphine, as well as any of its derivatives or analogs, may be used as a medicant in the invention of the present application.

Codeine is an opiate analgesic drug that is used to relieve moderate to severe pain. Like morphine it is an alkaloid found in opium. Like other opiates, codeine acts directly on the central nervous system (CNS) to relieve pain. Codeine has a high potential for addiction; tolerance and psychological dependence develop rapidly. It would be more effective, quicker acting and less likely to cause side effects if codeine was more quickly transported to the brain through the cardio-pulmonary system by ingesting and inhaling a vaporized product containing codeine. Accordingly, codeine may be used as a medicant in the invention of the present application.

Oxycodone is an opioid analgesic medication synthesized from poppy-derived thebaine. It was developed in 1916 in Germany, as one of several new semi-synthetic opioids in an attempt to improve on the existing opioids, morphine and codeine. Oxycodone oral medications are generally prescribed for the relief of moderate to severe pain. Currently it is formulated as single ingredient products or compounded products. Some common examples of compounding are oxycodone with acetaminophen/paracetamol or NSAIDs such as ibuprofen. The formulations are available as generics but are also made under various brand names.

Among the traditional methods or ingesting oxycodone is by mouth in various and readily available digestible compounds. It would be more effective, quicker acting and less likely to cause gastro-intestinal distress or side effects such as itching, nausea, vomiting, drowsiness, dry mouth, miosis, orthostatic hypotension, urinary retention, depression and constipation if oxycodone was more quickly transported to the brain through the cardio-pulmonary system by ingesting and inhaling a vaporized product containing oxycodone. Accordingly, oxycodone may be a medicant used in the invention of the present application.

When used for pain, inhaling an active ingredient, which is rapidly effective, may minimize a user from taking additional doses while waiting for pain relief. Such rapid effects may lead to lower dosing and less tendency to overmedicate, which may lead to less chance of addiction, and less complications from overmedication.

Appetite Suppressants

Appetite suppressants exist naturally in certain plants. For example, green tea and the hoodia plant are believed to contain active ingredients that can suppress appetite. Numerous other plants and chemical compounds are also believed to have appetite suppressant properties. However, it may not be practical to consume enough of these plant substances or extracts, such as green tea or hoodia, through the digestive system to feel the full effects. In addition, a rapidly-acting appetite suppressant may be beneficial in helping a user counteract sudden urges to eat. Accordingly, green tea, hoodia, and other appetite suppressant substances may be a medicant used in the invention of the present application, including with the extraction or leaching methods described herein.

Sexual Aids

Compounds for use as a sexual aid to help or enhance the performance of sexual function can also be used with the present invention, such as yohimbine, icariin, and type-5 phosphodiesterase (PDE-5) inhibitors.

Yohimbe is the principal alkaloid of the bark of a West Indian evergreen tree. It is used as a supplement to arouse sexual excitement, for erectile dysfunction (ED), sexual problems caused by medications for depression called selective-serotonin reuptake inhibitors (SSRIs), and general sexual problems in both men and women. It is also used for athletic performance, weight loss, exhaustion, chest pain, high blood pressure, low blood pressure that occurs when standing up, diabetic nerve pain, and for depression along with certain other medications. Yohimbe contains a chemical called yohimbine which can increase blood flow and nerve impulses to the penis or vagina. It also helps counteract the sexual side effects of certain medications used for depression. Yohimbe may be a medicant used in the invention of the present application.

Epimedium, also known as barrenwort, bishop's hat, fairy wings, horny goat weed, rowdy lamb herb, randy beef grass or yin yang huo, is a genus of flowering plants in the family Berberidaceae. Epimedium contains the active compound icariin, which like sildenafil, the active ingredient in Viagra, inhibits the activity of phosphodiesterase type 5 (PDE-5). However, the bioavailability via oral administration of this medicant is very low and the herb (and its active ingredient) would be much more effective when administered via vapor through the cardio-pulmonary system. Thus, there is a need for low temperature vaporization of the herb/medicant for ingestion via inhalation. As such, epimedium and the active compound icariin may be a medicant used in the invention of the present application.

PDE-5 inhibitors have been used to treat erectile dysfunction due to their ability to increase blood flow in the corpus cavernosum of the penis. In general, sexual stimulation results in nitric oxide release in the corpus cavernosum. Nitric oxide increases cyclic guanosine monophosphate (cGMP) levels, which results in smooth muscle relaxation in the arteries of the corpus cavernosum. Relaxation of the smooth muscle allows for increase in the blood flow in the corpus cavernosum resulting in an erection.

PDE-5 exists naturally in the walls of the smooth muscles of the corpus cavernosum. PDE-5, however, breaks down the cGMP that causes smooth muscle relaxation. Therefore, PDE-5 can restrict blood flow in the corpus cavernosum. PDE-5 inhibitors block the action of PDE-5, thereby increasing blood flow to the corpus cavernosum. A PDE-5 inhibitor taken orally as a pill can take an hour or more for its effect to take place. As such, some spontaneity is lost in using current forms of PDE-5 inhibitors.

As such, providing PDE-5 inhibitors via an inhalable vapor may restore some of the spontaneity in sexual activity by increasing the efficacy and speed with which PDE-5 inhibitors can take effect due to a more rapid uptake of the PDE-5 inhibitors through the lungs and into the cardiovascular system. In addition, grabbing a vaporization device and taking a quick puff is more convenient, faster, and easier than having to take pills out of a container, grabbing a glass of water, and then waiting for the effects to take place.

Examples of PDE-5 inhibitors include, but are not limited to, avanafil, sildenafil, tadalafil vardenafil, avanafil, lodenafil, mirodenafil, udenafil, zaprinast, icariin, benzamidenafil, and dasantafil.

In addition to use for erectile dysfunction, PDE-5 inhibitors may also have other uses. For example, since PDE-5 is also present in the smooth muscle of the lungs, PDE-5 inhibitors have been explored and used for the treatment of pulmonary hypertension, including but not limited to pulmonary arterial hypertension. PDE-5 inhibitors have also been used to alleviate vasospasm and to treat ischemia and ulcers in fingers and toes for people with secondary Raynaud's phenomenon. The uses of the PDE-5 inhibitors disclosed herein may not be limited to treating erectile dysfunction.

The categorization of the compounds described above is not meant to be limiting, but rather illustrative of the potential uses of the present invention. It is understood that some compounds disclosed herein can be used to treat other conditions within the spirit and scope of the present invention.

In addition, numerous other medicants can be used with the present invention. As such, the foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:

1. A method for delivering medicants through inhalation, comprising:
    a) acquiring a medicant solution suitable for vaporization, the medicant solution, comprising:
        i) an excipient comprising propylene glycol present at approximately 1 percent to approximately 30 percent of the excipient, vegetable glycerin present at approximately 1 percent to approximately 30 percent of the excipient, water present at approximately 0.01 percent to approximately 30 percent of the excipient, and alcohol present at approximately 0.01 percent to approximately 30 percent of the excipient, and
        ii) an alkaloid; and
    b) vaporizing the medicant solution at a temperature ranging from approximately 90 degrees C. to approximately 385 degrees C. such that an effective serving of the medicant solution is provided to a user for inhalation.

2. The method of claim 1, wherein the step of vaporizing the medicant solution comprises using a vaporizer.

3. A method for delivering medicants through inhalation, comprising:
    a) acquiring a liquid medicant solution suitable for vaporization, the liquid medicant solution, comprising:
        i) an excipient comprising an inert non-reactive compound, and
        ii) an alkaloid; and
    b) vaporizing the liquid medicant solution at a temperature ranging from approximately 90 degrees C. to approximately 120 degrees C., wherein the inert non-reactive compound is polysorbate, and wherein the step of vaporizing the medicant solution comprises using a low temperature vaporizer.

4. The method of claim 3, wherein the polysorbate is present at a concentration of at least about 1 percent of the excipient.

5. The method of claim 3, wherein the polysorbate is present at a concentration of at least about 10 percent of the excipient.

6. The method of claim 3, wherein the polysorbate is present at a concentration of at least about 30 percent of the excipient.

7. The method of claim 3, wherein the polysorbate is present at a concentration of at least about 70 percent of the excipient.

8. The method of claim 3, wherein the polysorbate is present at a concentration of at least about 85 percent of the excipient.

9. The method of claim 3, wherein the polysorbate comprises about 100 percent of the excipient.

10. The method of claim 3, wherein the excipient comprises any one or more polysorbate compound selected from the group consisting of polysorbate 20, polysorbate 40, polysorbate 60, and polysorbate 80.

11. A method for delivering medicants through inhalation, comprising:
   a) acquiring a liquid medicant solution suitable for vaporization, the liquid medicant solution, comprising:
      i) an excipient comprising an inert non-reactive compound, and
      ii) an alkaloid; and
   b) vaporizing the liquid medicant solution at a temperature ranging from approximately 170 degrees C. to approximately 200 degrees C., wherein the inert non-reactive compound is propylene glycol.

12. The method of claim 11, wherein the propylene glycol is present at a concentration of at least about 1 percent of the excipient.

13. The method of claim 11, wherein the propylene glycol is present at a concentration of at least about 10 percent of the excipient.

14. The method of claim 11, wherein the propylene glycol is present at a concentration of at least about 30 percent of the excipient.

15. The method of claim 11, wherein the propylene glycol is present at a concentration of at least about 70 percent of the excipient.

16. The method of claim 11, wherein the propylene glycol is present at a concentration of at least about 85 percent of the excipient.

17. The method of claim 11, wherein the propylene glycol comprises 100 percent of the excipient.

18. The method of claim 11, wherein the excipient further comprises glycerin.

* * * * *